US010065173B2

(12) United States Patent
Hinayama et al.

(10) Patent No.: US 10,065,173 B2
(45) Date of Patent: Sep. 4, 2018

(54) PROCESS FOR PRODUCING WATER-ABSORBENT RESIN

(71) Applicant: SUMITOMO SEIKA CHEMICALS CO., LTD., Kako-gun, Hyogo (JP)

(72) Inventors: Tetsuhiro Hinayama, Hyogo (JP); Masahiro Murakami, Hyogo (JP); Junichi Takatori, Hyogo (JP)

(73) Assignee: SUMITOMO SEIKA CHEMICALS CO., LTD., Kako-gun (JP)

( * ) Notice: Subject to any disclaimer, the term of this patent is extended or adjusted under 35 U.S.C. 154(b) by 0 days.

(21) Appl. No.: 14/759,762

(22) PCT Filed: Nov. 4, 2014

(86) PCT No.: PCT/JP2014/079267
§ 371 (c)(1),
(2) Date: Jul. 8, 2015

(87) PCT Pub. No.: WO2016/006135
PCT Pub. Date: Jan. 14, 2016

(65) Prior Publication Data
US 2016/0030919 A1   Feb. 4, 2016

(30) Foreign Application Priority Data

Jul. 11, 2014   (JP) ................. 2014-143609
Oct. 31, 2014   (JP) ................. 2014-223298

(51) Int. Cl.
| C08F 2/32 | (2006.01) |
| C08F 220/06 | (2006.01) |
| B01J 20/26 | (2006.01) |
| B01J 20/30 | (2006.01) |
| A61L 15/60 | (2006.01) |

(52) U.S. Cl.
CPC ............ B01J 20/261 (2013.01); A61L 15/60 (2013.01); B01J 20/3085 (2013.01); C08F 2/32 (2013.01); C08F 220/06 (2013.01)

(58) Field of Classification Search
CPC . C08F 2/32; C08F 20/06; C08F 220/06; C08J 3/243; C08J 3/245; C08J 2333/02
See application file for complete search history.

(56) References Cited

U.S. PATENT DOCUMENTS

| 5,624,967 | A | 4/1997 | Hitomi et al. |
| 5,798,176 | A | 8/1998 | Kitaori et al. |
| 5,981,070 | A | 11/1999 | Ishizaki et al. |
| 2004/0068057 | A1 | 4/2004 | Kim |
| 2009/0008604 | A1 | 1/2009 | Nakashima et al. |
| 2009/0318582 | A1 | 12/2009 | Loesch et al. |
| 2010/0062252 | A1 | 3/2010 | Kimura et al. |
| 2010/0062932 | A1* | 3/2010 | Losch ................. C08F 220/06 |
| | | | 502/402 |
| 2010/0240823 | A1* | 9/2010 | Sakamoto ............. A61L 15/60 |
| | | | 524/543 |
| 2012/0184670 | A1* | 7/2012 | Kobayashi ............ C08K 5/098 |
| | | | 524/556 |
| 2013/0175473 | A1 | 7/2013 | Wada et al. |
| 2013/0324396 | A1* | 12/2013 | Honda .................... C08F 6/006 |
| | | | 502/402 |
| 2013/0330566 | A1 | 12/2013 | Takatori |

FOREIGN PATENT DOCUMENTS

| CN | 102408505 A | 4/2012 |
| CN | 103429625 A | 12/2013 |
| EP | 0 288 865 A2 | 11/1988 |
| EP | 288 865 | * 11/1988 |
| EP | 1 882 701 A1 | 1/2008 |
| EP | 2 623 198 A1 | 8/2013 |
| EP | 2 692 744 A1 | 2/2014 |
| EP | 2 993 191 A1 | 3/2016 |
| EP | 2 998 325 A1 | 3/2016 |
| JP | 63-7203 A | 1/1988 |
| JP | 7-98847 A | 4/1995 |

(Continued)

OTHER PUBLICATIONS http://azobisamidinopropane-dihydrochloride.de/science_e.htm; "Scientific Data: Azo initiator"; 2003.*
https://en.wikipedia.org/wiki/Acrylate; 2016.*
EP 288 865, machine translation; 1988.*
International Search Report dated Feb. 10, 2015, issued in corresponding application No. PCT/JP2014/079267 (3 pages).
Matsumoto, Satoshi, "Certificate of Experimental Result", Superabsorbents Research Center, Nippon Shokubai Co., Ltd, with English translation, May 17, 2016; Japanese Ofice Action dated Aug. 10, 2016, (4 pages).
Extended (supplementary) European Search Report dated Apr. 19, 2016, issued in counterpart European Patent Application No. 14877553.9. (12 pages).
Office Action dated May 17, 2016, issued in counterpart Taiwanese Patent Application No. 104121453. (7 pages).

(Continued)

Primary Examiner — Roberto Rabago
(74) Attorney, Agent, or Firm — Westerman, Hattori, Daniels & Adrian, LLP

(57) ABSTRACT

The present invention provides a process for producing a water-absorbent resin, characterized in that a reverse-phase suspension polymerization of a water-soluble ethylenically unsaturated monomer is carried out in a hydrocarbon dispersion medium comprising a dispersion stabilizer while an azo-based compound and a peroxide are combined in the presence of an internal-crosslinking agent, in that the following formulae are satisfied, $$0.10 \leq B/(A+B) \quad (1), \text{ and}$$

$$0.055 \leq B + 9 \times C \leq 0.120 \quad (2),$$

wherein A mol, B mol and C mol represent used amounts of the azo-based compound, the peroxide and the internal-crosslinking agent, respectively, relative to 100 mol of the water-soluble ethylenically unsaturated monomer used in the polymerization, and in that a post-crosslinking reaction is carried out by adding a post-crosslinking agent after the polymerization. The present invention also relates to a water-absorbent resin having specific performance and produced by the process.

13 Claims, 1 Drawing Sheet

(56) References Cited

FOREIGN PATENT DOCUMENTS

| | | |
|---|---|---|
| JP | 8-188602 A | 7/1996 |
| JP | 11-335404 A | 12/1999 |
| JP | 2000-26510 A | 1/2000 |
| JP | 2003-238696 A | 8/2003 |
| JP | 3462217 B2 | 11/2003 |
| JP | 2004-517179 A | 6/2004 |
| JP | 2006-176570 A | 7/2006 |
| JP | 2006-219661 A | 8/2006 |
| JP | 2008-516007 A | 5/2008 |
| JP | 2008-133396 A | 6/2008 |
| JP | 2008-534693 A | 8/2008 |
| JP | 2006-297373 A | 5/2010 |
| JP | 2010-518208 A | 5/2010 |
| JP | 2012-236898 A | 12/2012 |
| WO | 2006/025586 A1 | 3/2006 |
| WO | 2006/088115 A1 | 8/2006 |
| WO | 2006/109844 A1 | 10/2006 |
| WO | 2006/109882 A1 | 10/2006 |
| WO | 2011/040472 A1 | 4/2011 |
| WO | 2012/043821 A | 4/2012 |
| WO | 2012/132861 A1 | 10/2012 |
| WO | 2012/132902 A1 | 10/2012 |
| WO | WO 2012/132861 A1 * | 10/2012 |
| WO | 2014/079710 A1 | 5/2014 |

OTHER PUBLICATIONS

Third Party Observation dated Jun. 13, 2016, filed in counterpart International Application No. PCT/JP2014/079267. (19 pages).

Notification of Transmittal of Translatioin of the International Preliminary Report on Patentability (Forms PCT/IB/338) issued in counterpart International Application No. PCT/JP2014/079267 dated Jan. 26, 2017 with Forms PCT/IB/373 and PCT/ISA/237 (8 pages).

Matsumoto, et al., Certificate of Experimental Result (WO 2012/132861), dated Nov. 10, 2015, with English translation. (2 pages).

Matsumoto, et al., Certificate of Experimental Result (WO 2012/043821), dated Nov. 10, 2015, with English translation. (3 pages).

Bucholz, et al. "Modern Superabsorbent Polymer Technology", ISBN 0-471194115. (8 pages), 1998.

Office Action dated Jan. 6, 2016, issued in counterpart Chinese Patent Application No. 201480003881.0. (6 pages).

* cited by examiner

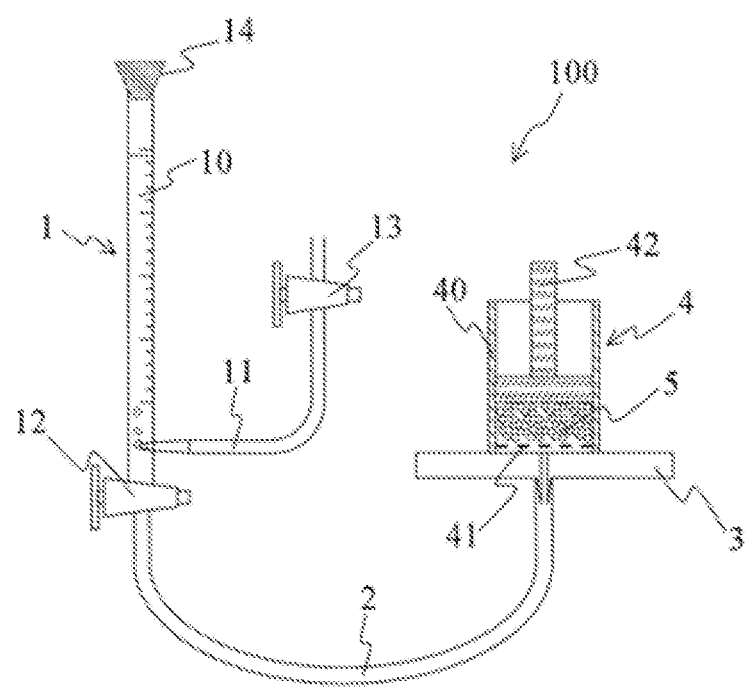

PROCESS FOR PRODUCING WATER-ABSORBENT RESIN

TECHNICAL FIELD

The present invention relates to a process for producing a water-absorbent resin. In more detail, the present invention relates to a process for producing a water-absorbent resin, wherein the water-absorbent resin has superior water-absorption performance including a high water-retention capacity, a high water-absorption capacity under a load and a high vertical diffusion water-absorption capacity, and has a decreased content of residual monomers, and wherein the water-absorbent resin is suitable for an absorbent article. The present invention also relates to a water-absorbent resin having specific performance and produced by the process, as well as an absorbent article comprising the resin.

BACKGROUND ART

A water-absorbent resin is widely used in recent years in a field of an absorbent article including hygienic materials such as disposable diapers and sanitary napkins; agricultural and horticultural materials such as a water-retention agent and a soil conditioner; industrial materials such as a water blocking agent and a dew condensation prevention agent. Although many kinds of water-absorbent resins have been known according to their uses, a water-absorbent resin made of a polymer of a water-soluble ethylenically unsaturated monomer is mainly used.

In a field of an absorbent article, particularly a hygiene product, in recent years, an absorbent material tends to be made thin so as to enhance comfort at use and portability. Methods for thinning an absorbent material include a method of increasing a ratio of a water-absorbent resin in an absorbent material; and a method of enhancing water-absorption performance (a water-retention capacity and a water-absorption capacity under a load) of a water-absorbent resin.

However, when the ratio of a water-absorbent resin in an absorbent material is increased, there is a concern for an effect on skin (skin rash) caused by unreacted monomers (residual monomers) contained in the water-absorbent resin.

On the other hand, in the water-absorbent resin made of a polymer of a water-soluble ethylenically unsaturated monomer, one option for achieving its high water-absorption performance is to decrease its crosslinking density. In view of easy control of polymerization reaction, in general, a persulfate is often used as a compound to be added in polymerization of a water-soluble ethylenically unsaturated monomer. However, a persulfate simultaneously promotes a self-crosslinking in polymerization reaction, and therefore, a crosslinking density inside a resin tends to increase, and it tends to be difficult to obtain a water-absorbent resin having high water-absorption performance. In order to solve this problem, a method has been proposed wherein a water-soluble azo-based radical initiator is used instead of a persulfate which tends to promote a self-crosslinking (see Patent Document 1).

However, when an azo-based compound is used, a large amount of residual monomers tend to exist in the resulting water-absorbent resin since it is difficult to increase the polymerization rate of a water-soluble ethylenically unsaturated monomer.

Some methods have been proposed for decreasing a content of residual monomers in a water-absorbent resin. For example, the following methods have been known; a method wherein two times or more of divided additions of a radical polymerization initiator to a monomer liquid are carried out to increase an amount of the initiator (see Patent Document 2); a method wherein a persulfate is added to a water-absorbent resin during or after polymerization (see Patent Document 3); and a method wherein a reducing substance is added to a water-absorbent resin before or during drying (see Patent Document 4); and the like.

PRIOR ART DOCUMENT

Patent Documents

Patent Document 1: JP 2006-176570 A
Patent Document 2: JP S63-7203 B
Patent Document 3: JP 2004-517179 A
Patent Document 4: JP H07-98847 B

SUMMARY OF THE INVENTION

Problem to be Solved by the Invention

In view that an absorbent article has suitable performance, that is, in view that a water-absorbent resin has a decreased content of residual monomers, as well as superior water-absorption performance desired for a water-absorbent resin, which includes a high water-retention capacity, a high water-absorption capacity under a load and a high vertical diffusion water-absorption capacity, these conventional technologies cannot provide a water-absorbent resin having satisfactory performance, and there is still room for further improvement.

The object of the present invention is to provide a process for producing a water-absorbent resin having a decreased content of residual monomers, and having a high water-retention capacity, a high water-absorption capacity under a load and a high vertical diffusion water-absorption capacity; a water-absorbent resin obtained by the process and having specific performance; as well as an absorbent article comprising the resin.

Means to Solve the Problems

The inventors have diligently studied to achieve the above object, and as a result, found that a water-absorbent resin having a decreased content of residual monomers, as well as a high water-retention capacity, a high water-absorption capacity under a load and a high vertical diffusion water-absorption capacity can be obtained by carrying out a reverse-phase suspension polymerization of a water-soluble ethylenically unsaturated monomer in a hydrocarbon dispersion medium comprising a dispersion stabilizer while an azo-based compound and a peroxide are combined in the presence of an internal-crosslinking agent, wherein the azo-based compound, the peroxide and the internal-crosslinking agent are each used in specific ratios, and the inventors has achieved the present invention.

The present invention provides the following process for producing a water-absorbent resin, water-absorbent resin obtained by the process and having specific performance, and absorbent article comprising the resin.

[1] A process for producing a water-absorbent resin, characterized in that a reverse-phase suspension polymerization of a water-soluble ethylenically unsaturated monomer is carried out in a hydrocarbon dispersion medium comprising a dispersion stabilizer while an azo-based compound and a peroxide are combined in the presence of an internal-crosslinking agent, in that the following formulae are satisfied, $$0.10 \leq B/(A+B) \tag{1}$$

and $$0.055 \leq B+9 \times C \leq 0.120 \tag{2}$$

wherein A mol, B mol and C mol represent used amounts of the azo-based compound, the peroxide and the internal-crosslinking agent, respectively, relative to 100 mol of the water-soluble ethylenically unsaturated monomer used in the polymerization, and in that a post-crosslinking reaction is carried out by adding a post-crosslinking agent after the polymerization.

[2] The process for producing a water-absorbent resin according to [1], wherein the azo-based compound is at least one selected from the group consisting of 2,2'-azobis(2-amidinopropane)dihydrochloride, 2,2'-azobis{2-[1-(2-hydroxyethyl)-2-imidazolin-2-yl]propane} dihydrochloride, and 2,2'-azobis[N-(2-carboxyethyl)-2-methylpropionamidine] tetrahydrate.

[3] The process for producing a water-absorbent resin according to [1], wherein the peroxide is at least one selected from the group consisting of potassium persulfate, ammonium persulfate, sodium persulfate and hydrogen peroxide.

[4] The process for producing a water-absorbent resin according to [1], wherein the internal-crosslinking agent is at least one selected from the group consisting of (poly) ethylene glycol diglycidyl ether, (poly)propylene glycol diglycidyl ether, (poly)glycerin diglycidyl ether and N,N'-methylenebis(meth)acrylamide.

[5] A water-absorbent resin obtained by polymerizing a water-soluble ethylenically unsaturated monomer in the presence of an internal-crosslinking agent, and adding a post-crosslinking agent after the polymerization to carry out a post-crosslinking reaction, wherein the water-absorbent resin satisfies all of the following characteristics (A) to (D):

(A) a water-retention capacity of physiological saline of 36 to 60 g/g, (B) a water-absorption capacity of physiological saline under a load of 4.14 kPa, of 15 ml/g or higher, (C) a vertical diffusion water-absorption capacity of 4.0 ml/g or higher, and (D) a content of residual monomers of 180 ppm or lower.

[6] An absorbent article comprising the water-absorbent resin according to [5].

Effect of the Invention

The present invention can provide a process for producing a water-absorbent resin having a decreased content of residual monomers, as well as a high water-retention capacity, a high water-absorption capacity under a load and a high vertical diffusion water-absorption capacity. Thus, the present invention can provide a water-absorbent resin which has specific performance suitable for an absorbent article, and an absorbent article comprising the resin.

BRIEF DESCRIPTION OF DRAWINGS

FIG. 1 is a pattern diagram representing a schematic arrangement of an apparatus for measuring a water-absorption capacity of physiological saline under a load of 4.14 kPa and a vertical diffusion water-absorption capacity.

MODES FOR CARRYING OUT THE INVENTION

The production process of the present invention is characterized in that, when a reverse-phase suspension polymerization of a water-soluble ethylenically unsaturated monomer is carried out in a hydrocarbon dispersion medium comprising a dispersion stabilizer while an azo-based compound and a peroxide are combined in the presence of an internal-crosslinking agent, the azo-based compound, the peroxide and the internal-crosslinking agent are each used in specific ratios.

The production process of the present invention is characterized in that the following formulae are satisfied, $$0.10 \leq B/(A+B) \tag{1}$$

and $$0.055 \leq B+9 \times C \leq 0.120 \tag{2}$$

wherein A mol, B mol and C mol represent used amounts of the azo-based compound, the peroxide and the internal-crosslinking agent, respectively, relative to 100 mol of the water-soluble ethylenically unsaturated monomer used in the polymerization.

In view of decreasing the content of residual monomers in the water-absorbent resin, the value of formula (1) is 0.10 or higher, preferably 0.15 or higher, and more preferably 0.20 or higher. On the other hand, in view of achieving a high water-retention capacity and a high water-absorption capacity under a load of the water-absorbent resin, the value of formula (1) is preferably 0.50 or lower, more preferably 0.45 or lower, and further preferably 0.40 or lower.

In view of enhancing liquid permeability and liquid suction ability of the water-absorbent resin, that is, a vertical diffusion water-absorption capacity, the value of formula (2) is 0.055 or higher, preferably 0.058 or higher, and more preferably 0.060 or higher. On the other hand, in view of achieving a high water-retention capacity and a high water-absorption capacity under a load of the water-absorbent resin, the value of formula (2) is 0.120 or lower, preferably 0.110 or lower, and further preferably 0.100 or lower.

In the production process of the present invention, a combined use of an azo-based compound and a peroxide refers to a condition where the azo-based compound and the peroxide do not necessarily simultaneously coexist at the start time point of polymerization reaction and where one compound exists while a monomer conversion ratio caused by radical cleavage of another compound is less than 10%, and preferably refers to a condition where both of these compounds simultaneously coexist in an aqueous solution comprising a monomer before the start time point of polymerization reaction. The azo-based compound and the peroxide may be added to the polymerization system through different separate fluid channels or may be serially added to the polymerization system through one fluid channel. Each of the azo-based compound and peroxide used may be in the form of a powder or an aqueous solution.

Examples of the azo-based compound used in the production process of the present invention include such compounds as 1-{1-cyano-1-methylethyl)azo} formamide, 2,2'-azobis[2-(N-phenylamidino)propane] dihydrochloride, 2,2'-azobis{2-[N-(4-chlorophenyl)amidino]propane} dihydrochloride, 2,2'-azobis{2-[N-(4-hydroxyphenyl)amidino]propane} dihydrochloride, 2,2'-azobis[2-(N-benzylamidino)propane] dihydrochloride, 2,2'-azobis[2-(N-allylamidino)propane] dihydrochloride, 2,2'-azobis(2-amidinopropane) dihydrochloride, 2,2'-azobis{2-[N-(2-hydroxyethyl)amidino]propane} dihydrochloride, 2,2'-azobis[2-(5-methyl-2-imidazolin-2-yl)propane] dihydrochloride, 2,2'-azobis[2-(2-imidazolin-2-yl)propane] dihydrochloride, 2,2'-azobis[2-(4,5,6,7-tetrahydro-1H-1,3-diazepin-2-yl)propane] dihydrochloride, 2,2'-azobis[2-(5-hydroxy-3,4,5,6-tetrahydropyrimidin-2-yl) propane] dihydrochloride, 2,2'-azobis{2-[1-(2-hydroxyethyl)-2-imidazolin-2-yl]propane} dihydrochloride, 2,2'-azobis[2-(2-imidazolin-2-yl)propane], 2,2'-azobis{2-methyl-N-[1,1-bis(hydroxymethyl)-2-hydroxyethyl] propionamide}, 2,2'-azobis{2-methyl-N-[1,1-bis(hydroxymethyl)ethyl] propionamide}, 2,2'-azobis[2-methyl-N-(2-hydroxyethyl) propionamide], 2,2'-azobis(2-methylpropionamide) dihydrochloride, 4,4'-azobis-4-cyanovaleric acid, 2,2'-azobis[2-(hydroxymethyl) propionitrile], 2,2'-azobis[2-(2-imidazolin-2-yl)propane] disulfate dihydrate, 2,2'-azobis[N-(2-carboxyethyl)-2-methylpropionamidine] tetrahydrate, and 2,2'-azobis[2-methyl-N-(2-hydroxyethyl) propionamide]. Among them, 2,2'-azobis(2-amidinopropane)dihydrochloride, 2,2'-azobis{2-[1-(2-hydroxyethyl)-2-imidazolin-2-yl]propane} dihydrochloride, and 2,2'-azobis[N-(2-carboxyethyl)-2-methylpropionamidine] tetrahydrate are preferable, in view that polymerization reaction control such as polymerization temperature is easy and that a water-absorbent resin having a high water-retention capacity and a high water-absorption capacity under a load can be obtained. The azo-based compound may be used alone or in combination of two or more kinds.

Within the range of formula (1), the used amount A mol of the azo-based compound is preferably from 0.005 to 1 mol, relative to 100 mol of the water-soluble ethylenically unsaturated monomer used in the polymerization, in view that a rapid polymerization reaction is prevented and that polymerization reaction time can be shortened.

Examples of the peroxide used in the production process of the present invention include persulfates such as potassium persulfate, ammonium persulfate and sodium persulfate; hydrogen peroxide; and organic peroxides such as methyl ethyl ketone peroxide, methyl isobutyl ketone peroxide, di-t-butyl peroxide, t-butyl cumyl peroxide, t-butyl peroxyacetate, t-butylperoxyisobutylate and t-butyl peroxypivalate. Among them, in view of easy availability and handling, potassium persulfate, ammonium persulfate, sodium persulfate and hydrogen peroxide are preferable, and potassium persulfate, ammonium persulfate and sodium persulfate are more preferable.

Within the ranges of formulae (1) and (2), the used amount B mol of the peroxide is preferably from 0.0005 to 0.10 mol, relative to 100 mol of the water-soluble ethylenically unsaturated monomer used in the polymerization.

Examples of the internal-crosslinking agent used in the production process of the present invention include unsaturated polyesters obtained by reacting a polyol including a diol and a triol such as (poly)ethylene glycol ("(poly)" refers to a case where a prefix "poly" exists and a case where the prefix does not exist. The same applies to the following), (poly)propylene glycol, 1,4-butane diol, trimethylolpropane and (poly)glycerin, with an unsaturated acid such as (meth)acrylic acid (within the context of the present invention, "(meth)acryl" refers to "acryl" or "methacryl". The same applies to the following), maleic acid and fumaric acid; bis(meth)acrylamides such as N,N'-methylenebis(meth)acrylamide; di- or tri-(meth)acrylic acid esters obtained by reacting polyepoxide with (meth)acrylic acid; di(meth)acrylic acid carbamyl esters obtained by reacting polyisocyanate, such as tolylene diisocyanate and hexamethylene diisocyanate, with hydroxyethyl(meth)acrylic acid; compounds having two or more of polymerizable unsaturated groups such as allylated starch, allylated cellulose, diallylphthalate, N,N',N''-triallyl isocyanate and divinylbenzene; polyglycidyl compounds including diglycidyl compounds and triglycidyl compounds, such as (poly)ethylene glycol diglycidyl ether, (poly)propylene glycol diglycidyl ether and (poly)glycerin diglycidyl ether; epihalohydrin compounds such as epichlorohydrin, epibromohydrin, α-methyl epichlorohydrin; isocyanate compounds such as 2,4-tolylene diisocyanate and hexamethylene diisocyanate; compounds having two or more of reactive groups including oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol and 3-butyl-3-oxetane ethanol. Among them, in view of superior reactivity under a low temperature, (poly)ethylene glycol diglycidyl ether, (poly)propylene glycol diglycidyl ether, (poly)glycerin diglycidyl ether and N,N'-methylenebisacrylamide are preferable. The internal-crosslinking agent may be used alone or in combination of two or more kinds.

Within the range of formula (2), the used amount C mol of the internal-crosslinking agent is preferably from 0.001 to 0.013 mol, relative to 100 mol of the water-soluble ethylenically unsaturated monomer used in the polymerization.

In the production process of the present invention, a reverse-phase suspension polymerization of a water-soluble ethylenically unsaturated monomer is carried out in a hydrocarbon dispersion medium comprising a dispersion stabilizer under the above-mentioned conditions to produce a water-absorbent resin.

In the present invention, the reverse-phase suspension polymerization may be carried out in a single stage or in multi-stages having two or more stages. In multi-stage polymerization having two or more stages, the particle size of the water-absorbent resin can be increased by agglomerating the water-absorbent resin obtained in the first stage of a reverse-phase suspension polymerization, and thus, it is easier to obtain the appropriate particle size thereof, which is suitable for absorbent articles such as disposable diapers, for example.

In case where two or more stages of reverse-phase suspension polymerization are carried out, after the first stage of reverse-phase suspension polymerization is carried out, a water-soluble ethylenically unsaturated monomer is added to the reaction product obtained in the first stage of polymerization reaction and mixed, and then, the second stage of reverse-phase suspension polymerization may be carried out in the same way as in the first stage. In each stage of the second and higher stages of reverse-phase suspension polymerization, it is preferable that, in addition to the water-soluble ethylenically unsaturated monomer, the azo-based compound, peroxide and internal-crosslinking agent are added in the above-mentioned molar ratio ranges of each components relative to the water-soluble ethylenically unsaturated monomer, based on the amount of the water-soluble ethylenically unsaturated monomer to be added in each stage of the second and higher stages of reverse-phase suspension polymerization, so as to carry out reverse-phase suspension polymerization in the similar conditions.

Examples of the water-soluble ethylenically unsaturated monomer used in the present invention include (meth)acrylic acid and the salt thereof; 2-(meth)acrylamide-2-methylpropanesulfonic acid and the salt thereof; non-ionic monomers such as (meth)acrylamide, N,N-dimethyl(meth)acrylamide, 2-hydroxyethyl(meth)acrylate, N-methylol (meth)acrylamide and polyethylene glycol mono(meth)acrylate; and amino group-containing unsaturated monomers such as N,N-diethylaminoethyl(meth)acrylate, N,N-diethylaminopropyl (meth)acrylate and diethylaminopropyl (meth)acrylamide, as well as the quaternary compounds thereof. The water-soluble ethylenically unsaturated monomer may be used alone or in combination of two or more kinds.

Among them, in view of industrially easy availability, (meth)acrylic acid and the salt thereof, (meth)acrylamide, N,N-dimethylacrylamide are preferable, and (meth)acrylic acid and the salt thereof are more preferable.

In case where two or more stages of reverse-phase suspension polymerization are carried out in multi-stages, a water-soluble ethylenically unsaturated monomer used in the second and higher stages may be identical to or different from a water-soluble ethylenically unsaturated monomer used in the first stage.

When a reverse-phase suspension polymerization is carried out, the above-mentioned water-soluble ethylenically unsaturated monomer may be also in the form of an aqueous solution so as to increase its dispersion efficiency in the hydrocarbon dispersion medium. By making the monomer in the form of an aqueous solution, its dispersion efficiency in the hydrocarbon dispersion medium can be increased. The concentration of the water-soluble ethylenically unsaturated monomer in this aqueous solution is preferably in a range of 20 mass % to saturated concentration. In polymerization in the presence of an azo-based compound, a polymerization rate tends to increase. Thus, in view that excessive heat accumulation is avoided and simultaneously that the performance of the water-absorbent resin according to the present invention is easily obtained, the concentration of the monomer is more preferably 55 mass % or lower, further preferably 50 mass % or lower, and further more preferably 45 mass % or lower. On the other hand, in order to maintain its productivity at a suitable level, the concentration of the monomer is more preferably 25 mass % or higher, further preferably 28 mass % or higher, and further more preferably 30 mass % or higher.

When the water-soluble ethylenically unsaturated monomer has an acidic group such as (meth)acrylic acid and 2-(meth)acrylamide-2-methylpropanesulfonic acid, the acidic group may be preliminarily neutralized with an alkaline neutralizer if necessary. Examples of the alkaline neutralizer include alkali metal salt such as sodium hydroxide, sodium carbonate, sodium hydrogen carbonate, potassium hydroxide and potassium carbonate; and ammonia. In particular, the alkaline neutralizer may be used in the form of an aqueous solution so as to simplify neutralization treatment. The alkaline neutralizer may be used alone or in combination of two or more kinds.

Usually, as to the degree of neutralization of the water-soluble ethylenically unsaturated monomer with the alkaline neutralizer, in view that the osmotic pressure of the obtained water-absorbent resin is increased to enhance its water-absorption performance, and that some problems in respect to safety or the like do not occur due to existence of an excess of the alkaline neutralizer, the degree of neutralization, which is based on all of the acidic groups contained in the water-soluble ethylenically unsaturated monomer, is preferably from 10 to 100 mol %, more preferably from 30 to 90 mol %, further preferably from 40 to 85 mol %, and further more preferably from 50 to 80 mol %.

Examples of the hydrocarbon dispersion medium used in the production process of the present invention include aliphatic hydrocarbons having 6 to 8 carbon atoms such as n-hexane, n-heptane, 2-methylhexane, 3-methylhexane, 2,3-dimethylpentane, 3-ethylpentane and n-octane; cycloaliphatic hydrocarbons such as cyclohexane, methylcyclohexane, cyclopentane, methylcyclopentane, trans-1,2-dimethylcyclopentane, cis-1,3-dimethylcyclopentane and trans-1,3-dimethylcyclopentane; and aromatic hydrocarbons such as benzene, toluene and xylene. The hydrocarbon may be used alone or in combination of two or more kinds.

Among the hydrocarbon dispersion media, in view of industrially easy availability, stable quality and low cost, n-hexane, n-heptane and cyclohexane are preferable. In addition, examples of a mixture of the above-mentioned hydrocarbon dispersion media include EXXSOL Heptane, which is commercially available (manufactured by Exxon Mobil Corporation: which contain 75 to 85 mass % of heptane and its isomeric hydrocarbon), and suitable result can be obtained therewith.

In view of removal of the heat of polymerization and easy control of polymerization temperature, the used amount of the hydrocarbon dispersion medium is, relative to 100 parts by mass of the water-soluble ethylenically unsaturated monomer used in the first stage of polymerization, preferably from 100 to 1500 parts by mass, and more preferably from 200 to 1400 parts by mass. The first stage of polymerization refers to a step of a single-stage polymerization, and a step of a first stage in multi-stage polymerization having two or more stages.

A surfactant may be used as the dispersion stabilizer used in the production process of the present invention, and examples thereof include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde-condensed polyoxyethylene ethers, polyoxyethylene polyoxypropylene block copolymers, polyoxyethylene polyoxypropyl alkyl ethers, polyethylene glycol fatty acid esters, alkylglucosides, N-alkylgluconamides, polyoxyethylene fatty acid amides, polyoxyethylene alkylamines, phosphoric acid esters of polyoxyethylene alkyl ethers, and phosphoric acid esters of polyoxyethylene alkylallyl ethers. Among them, in view of dispersion stability of monomers, sorbitan fatty acid esters, polyglycerin fatty acid esters and sucrose fatty acid esters are preferable. The surfactant may be used alone or in combination of two or more kinds.

The used amount of the surfactant is, relative to 100 parts by mass of the water-soluble ethylenically unsaturated monomer used in the first stage of polymerization, preferably from 0.1 to 30 parts by mass, and more preferably from 0.3 to 20 parts by mass, in view of maintaining suitable dispersion condition of monomers in a hydrocarbon dispersion medium and obtaining dispersion effect commensurate with the used amount.

As the dispersion stabilizer, a polymeric dispersion agent may be also combined with the surfactant. Examples of a usable polymeric dispersion agent include maleic anhydride-modified polyethylene, maleic anhydride-modified polypropylene, maleic anhydride-modified ethylene.propylene copolymer, maleic anhydride-modified EPDM (ethylene.propylene.diene.terpolymer), maleic anhydride-modified polybutadiene, maleic anhydride.ethylene copolymer, maleic anhydride.propylene copolymer, maleic anhydride-.ethylene.propylene copolymer, maleic anhydride.butadiene copolymer, polyethylene, polypropylene, ethylene.propylene copolymer, oxidation type polyethylene, oxidation type polypropylene, oxidation type ethylene.propylene copolymer, ethylene.acrylic acid copolymer, ethyl cellulose and ethylhydroxyethyl cellulose. Among them, in view of dispersion stability of monomers, maleic anhydride-modified polyethylene, maleic anhydride-modified polypropylene, maleic anhydride-modified ethylene.propylene copolymer, maleic anhydride.ethylene copolymer, maleic anhydride.propylene copolymer, maleic anhydride.ethylene.propylene copolymer, polyethylene, polypropylene, ethylene.propylene copolymer, oxidation type polyethylene, oxidation type polypropylene and oxidation type ethylene.propylene copolymer are preferable. The polymeric dispersion agent may be used alone or in combination of two or more kinds.

The used amount of the polymeric dispersion agent is, relative to 100 parts by mass of the water-soluble ethylenically unsaturated monomer in a first stage, preferably from 0.1 to 30 parts by mass, and more preferably from 0.3 to 20 parts by mass, in view of maintaining suitable dispersion condition of monomers in a hydrocarbon dispersion medium and obtaining dispersion effect commensurate with the used amount.

In view of quickly proceeding polymerization and shortening the polymerization time to increase productivity, and simultaneously removing the heat of polymerization to smoothly carry out the reaction, the reaction temperature of the reverse-phase suspension polymerization is preferably from 20 to 110° C., and more preferably from 40 to 90° C. The reaction time is preferably from 0.1 to 4 hours.

According to the production process of the present invention, it is possible to obtain water-containing gel in the form of moderately sized particle, and thereby obtain a water-absorbent resin in the form of moderately sized particle suitable for producing an absorbent article.

In the production process of the present invention, post-crosslinking reaction is carried out by adding a post-crosslinking agent after the polymerization of the water-soluble ethylenically unsaturated monomer. By carrying out the post-crosslinking reaction after the polymerization, it is possible to further enhance a water-retention capacity and a water-absorption performance.

Examples of the crosslinking agent used in the post-crosslinking reaction (post-crosslinking agent) include polyols such as ethylene glycol, propylene glycol, 1,4-butane diol, trimethylolpropane, glycerin, polyoxyethylene glycol, polyoxypropylene glycol and polyglycerin; polyglycidyl compounds such as (poly)ethylene glycol diglycidyl ether, (poly)glycerin diglycidyl ether, (poly)glycerin triglycidyl ether, (poly)propylene glycol polyglycidyl ether, (poly)glycerol polyglycidyl ether and trimethylolpropane triglycidyl ether; haloepoxy compounds such as epichlorohydrin, epibromohydrin and α-methylepichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol and 3-butyl-3-oxetane ethanol; oxazoline compounds such as 1,2-ethylenebisoxazoline; carbonate compounds such as ethylene carbonate; and hydroxyalkyl amide compounds such as bis[N,N-di(β-hydroxyethyl)]adipamide. Among the post-crosslinking agents, polyglycidyl compounds such as (poly)ethylene glycol diglycidyl ether, (poly)glycerin diglycidyl ether, (poly)glycerin triglycidyl ether, (poly)propylene glycol polyglycidyl ether and (poly)glycerol polyglycidyl ether are preferably used. The post-crosslinking agent may be used alone or in combination of two or more kinds.

The used amount of the post-crosslinking agent is, relative to 100 mol of the water-soluble ethylenically unsaturated monomer used in the polymerization, preferably from 0.001 to 1 mol, and more preferably from 0.005 to 0.5 mol.

The post-crosslinking agent is added after the polymerization reaction of the water-soluble ethylenically unsaturated monomer is almost completed. The post-crosslinking agent is preferably added in the presence of water in the range of 1 to 400 parts by mass, more preferably added in the presence of water in the range of 5 to 200 parts by mass, further preferably added in the presence of water in the range of 10 to 100 parts by mass, and further more preferably added in the presence of water in the range of 20 to 60 parts by mass, relative to 100 parts by mass of the water-soluble ethylenically unsaturated monomer used to obtain a water-absorbent resin.

Examples of a method for adding the post-crosslinking agent include a method of directly adding the post-crosslinking agent, a method of adding the post-crosslinking agent in the form of an aqueous solution, and a method of adding the post-crosslinking agent in the form of solution with a hydrophilic organic solvent as a solvent. Examples of the hydrophilic organic solvent include lower alcohols such as methyl alcohol, ethyl alcohol, n-propyl alcohol and isopropyl alcohol; ketones such as acetone and methyl ethyl ketone; ethers such as diethyl ether, dioxane and tetrahydrofuran; amides such as N,N-dimethyl formamide; and sulfoxides such as dimethyl sulfoxide. The hydrophilic organic solvent may be used alone, in combination of two or more kinds, or in admixture with the water as necessary.

The reaction temperature of the post-crosslinking reaction is preferably from 50 to 250° C., more preferably from 60 to 180° C., and further preferably from 70 to 150° C. The reaction time of the post-crosslinking reaction is preferably from 1 to 300 minutes, and more preferably from 5 to 200 minutes.

The production process of the present invention may comprise drying treatment of removing water, a hydrocarbon dispersion medium or the like via distillation by externally adding energy such as heat after completion of the polymerization. The drying treatment may be carried out under normal pressure, under reduced pressure or under gas stream such as nitrogen stream in order to enhance drying efficiency, or the combination thereof may be employed. The drying temperature in case of the drying treatment under normal pressure is preferably from 70 to 250° C., more preferably from 80 to 180° C., and further preferably from 80 to 140° C. The drying temperature in case of the drying treatment under reduced pressure is preferably from 40 to 160° C., and more preferably from 50 to 120° C.

It is possible to obtain a water-absorbent resin composition by combining the water-absorbent resin obtained by the production process of the present invention with various additives for various purposes so as to provide a specific ability. Examples of the additives include an inorganic powder, a surfactant, an oxidant, a reducing agent, a metal chelating agent, a radial chain inhibitor, an antioxidant, an anti-bacterial agent and a deodorant. For example, it is possible to enhance flowability of the water-absorbent resin by adding 0.05 to 5 parts by mass of amorphous silica, relative to 100 parts by mass of the water-absorbent resin.

The production process of the present invention can provide a water-absorbent resin having specific performance suitable for an absorbent article, which includes a decreased content of residual monomers, as well as a high water-retention capacity, a high water-absorption capacity under a load and a high vertical diffusion water-absorption capacity.

The water-retention capacity of physiological saline, water-absorption capacity of physiological saline under a load of 4.14 kPa, vertical diffusion water-absorption capacity, content of residual monomers and median particle size, of a water-absorbent resin, are measured in the following measurement methods.

The water-retention capacity of physiological saline of the water-absorbent resin of the present invention is, in view of increasing absorption volume and decreasing re-wet amount of a liquid when the resin is used in an absorbent article, preferably from 36 to 60 g/g, more preferably from 38 to 58 g/g, further preferably from 40 to 56 g/g, and further more preferably from 42 to 54 g/g.

The water-absorption capacity of physiological saline under a load of 4.14 kPa of the water-absorbent resin of the present invention is, in view of decreasing re-wet amount of a liquid when an absorbent article after liquid absorption is pressed in case that the resin is used in the absorbent article, preferably 15 ml/g or higher, more preferably from 16 to 40 ml/g, further preferably from 18 to 35 ml/g, and further more preferably from 20 to 32 ml/g.

The vertical diffusion water-absorption capacity of the water-absorbent resin of the present invention is, in view of increasing liquid diffusivity when the resin is used in an absorbent article, preferably 4.0 ml/g or higher, more preferably from 5.0 to 50.0 ml/g, further preferably from 6.0 to 30.0 ml/g, and further more preferably from 7.0 to 20.0 ml/g.

The content of residual monomers of the water-absorbent resin of the present invention is, in view of reducing an effect on skin (skin rash) when the resin is used in an absorbent article, preferably 180 ppm or lower, more preferably 150 ppm or lower, further preferably 100 ppm or lower, and further more preferably 90 ppm or lower, per mass of the water-absorbent resin.

The median particle size of a water-absorbent resin of the present invention is, in view of avoiding gel-blocking in liquid absorption due to fine particles and avoiding deterioration of touch feeling of an absorbent article due to coarse particles in case where the resin is used in the absorbent article, preferably from 100 to 600 μm, more preferably from 200 to 500 μm, further preferably from 250 to 450 μm, and further more preferably from 300 to 430 μm.

The absorbent article obtained in the present invention is not particularly limited. Typical examples thereof include hygienic materials such as disposable diapers, sanitary napkins, panty liners, incontinence pads and breast milk pads; urine-absorbent materials for pets; materials for civil engineering and construction such as packing materials; food freshness preservatives such as drip absorption materials and refrigerants; and agricultural and horticultural materials such as a water-retention agent for a soil.

For example, an absorbent article to be used for a hygienic material has such a constitution that an absorbent material, which absorbs and retains an aqueous liquid, is retained between a liquid permeable sheet (top sheet), through which the aqueous liquid can go, and a liquid impermeable sheet (back sheet), through which the aqueous liquid cannot go. The liquid permeable sheet is located on the side which contacts a body, and the liquid impermeable sheet is located on the side which does not contact a body.

Examples of the liquid permeable sheet include nonwovens of air-through type, spunbond type, chemical bond type, needle-punched type and the like, which are made of a fiber of polyethylene, polypropylene, polyester or the like, as well as porous synthetic resin sheet.

Examples of the liquid impermeable sheet include synthetic resin films made of a resin such as polyethylene, polypropylene and polyvinyl chloride.

The absorbent material used in the absorbent article is constituted with the water-absorbent resin obtained in the present invention and a hydrophilic fiber. Examples of a constitution of the absorbent material include a mixed dispersion obtained by mixing the water-absorbent resin and the hydrophilic fiber so that their composition is uniform; a sandwiched structure wherein the water-absorbent resin is held between layered hydrophilic fibers; and a structure wherein the water-absorbent resin and hydrophilic fiber are wrapped with a tissue, a permeable nonwoven or the like.

Other components including an adhesive binder such as a thermally adhesive fiber, a hot melt adhesive agent and an adhesive emulsion, for increasing a shape retention property of the absorbent material, may be also added to the absorbent material.

Examples of the hydrophilic fiber include cellulose fibers prepared from wood, such as cotton-like pulp, mechanical pulp, chemical pulp and semi-chemical pulp; artificial cellulose fibers such as rayon and acetate; and fibers made of synthetic resins such as hydrophilization-treated polyamides, polyesters and polyolefins.

EXAMPLES

The present invention is described below in further detail on the basis of Examples and Comparative Examples. However, the present invention is not limited to these Examples.

A water-retention capacity of physiological saline, a water-absorption capacity of physiological saline under a load of 4.14 kPa, a vertical diffusion water-absorption capacity, a content of residual monomers and a median particle size, of a water-absorbent resin obtained in each of Examples and Comparative Examples, were measured in the following measurement methods.

<Water-Retention Capacity of Physiological Saline>

In a 500-mL beaker, 500 g of 0.9 mass %-aqueous sodium chloride solution (physiological saline) was weighed, and 2.0 g of a water-absorbent resin was dispersed under stirring at 600 rotations/min so that lumps were not generated. The water-absorbent resin was left to stand under stirring for 30 minutes to fully swell. Subsequently, the dispersion was poured to a cotton bag (cotton broad cloth No. 60, height 100 mm×width 200 mm), and the top part of the cotton bag was bound with a rubber band. Then, the cotton bag was dehydrated for one minute by means of a dehydrator (manufactured by KOKUSAN Co., Ltd.; product number: H-122) whose centrifugal force was set at 167 G, and the mass Wa (g) of the cotton bag containing swollen gel after dehydration was measured. The same operation was carried out without pouring a water-absorbent resin, and an empty mass Wb (g) of the cotton bag in wetting was measured. A water-retention capacity of physiological saline of the water-absorbent resin was calculated according to the following formula.

Water-retention Capacity of Physiological saline(g/g)=[$Wa-Wb$](g)/Mass of Water-absorbent Resin(g)

<Water-Absorption Capacity of Physiological Saline Under a Load of 4.14 kPa>

A water-absorption capacity of physiological saline under a load of 4.14 kPa was measured with Measurement device 100 whose pattern diagram was represented in FIG. 1.

Measurement device 100 represented in FIG. 1 consists of Burette part 1, Conduit 2, Measurement table 3, and Measurement part 4 located on Measurement table 3. In Burette part 1, Rubber stopper 14 is connected to a top part of Burette 10, and Air introduction pipe 11 and Cock 12 are connected to a lower part of Burette 10. There is Cock 13 on a top part of Air introduction pipe 11. Conduit 2 is arranged between Burette part 1 and Measurement table 3, and the diameter of Conduit 2 is 6 mm. Measurement table 3 has a hole having a diameter of 2 mm on its central part, to which Conduit 2 is connected. Measurement part 4 has Cylinder 40, Nylon mesh 41, which is stuck on a bottom part of Cylinder 40, and Weight 42. The internal diameter of Cylinder 40 is 2.0 cm. A specific amount of Water-absorbent resin 5 is to be uniformly scattered on Nylon mesh 41 of 200-mesh (opening size 75 μm). Weight 42 has a diameter of 1.9 cm and a mass of 119.6 g. Weight 42 is located on Water-absorbent resin 5, and can uniformly provide a load of 4.14 kPa to Water-absorbent resin 5.

In Measurement device 100 having such a constitution, Cock 12 and Cock 13 of Burette part 1 are firstly closed, and a physiological saline, whose temperature is adjusted to 25° C., is poured from the top part of Burette 10. After the top part of Burette is covered with Rubber stopper 14, Cock 12 and Cock 13 of Burette part 1 are opened. Then, the height of Measurement table 3 is adjusted so that height of an end part of Conduit 2 in the central part of Measurement table 3 is identical to height of an air introduction port of Air introduction pipe 11.

In addition, 0.10 g of Water-absorbent resin 5 is uniformly scattered on Nylon mesh 41 in Cylinder 40, and Weight 42 is placed on Water-absorbent resin 5. Measurement part 4 is placed so that its central part coincides with a port of the conduit in the central part of Measurement table 3.

A volume decrease of physiological saline in Burette 10 (an amount of physiological saline which was absorbed by Water-absorbent resin 5), Wc (ml), was continuously read off from the time point when Water-absorbent resin 5 began to absorb the physiological saline. A water-absorption capacity of physiological saline under load of 4.14 kPa, of Water-absorbent resin 5 after 60 minutes from beginning of absorption, was determined according to the following formula.

Water-absorption Capacity of Physiological saline under a Load of 4.14 kPa(ml/g)=$Wc$(ml)/Mass of Water-absorbent Resin(g)

<Vertical Diffusion Water-Absorption Capacity>

A vertical diffusion water-absorption capacity was measured with Measurement device 100, whose pattern diagram was represented in FIG. 1, in the same method as in the water-absorption capacity of physiological saline under load of 4.14 kPa except that Weight 42 was not used and that the used amount of Water-absorbent resin 5 was changed to 1.0 g.

A volume decrease of physiological saline in Burette 10 (an amount of physiological saline which was absorbed by Water-absorbent resin 5), Wd (ml), was continuously read off from the time point when Water-absorbent resin 5 began to absorb the physiological saline. A vertical diffusion water-absorption capacity of Water-absorbent resin 5 after 60 minutes from beginning of absorption was determined according to the following formula.

Vertical Diffusion Water-absorption Capacity(ml/g)=$Wd$(ml)/Mass of Water-absorbent Resin(g)

<Content of Residual Monomers>

In a 500-mL beaker, 500 g of physiological saline was poured, and 2.0 g of a water-absorbent resin was added thereto and stirred at 600 rotations/min for 60 minutes. The dispersion in the beaker was filtered by means of a JIS standard sieve having an opening size of 75 μm and a filter paper (manufactured by ADVANTEC; Filter paper No. 3) to separate into water-absorbing gel and an extraction liquid. A content of monomers dissolving in the obtained extraction liquid was measured with a high-performance liquid chromatography. The measured value was converted to a value per mass of the water-absorbent resin, which was defined as a content (unit: ppm) of residual monomers in a water-absorbent resin.

<Median Particle Size>

0.25 g of amorphous silica (Degussa Japan Co., Ltd.; Sipernat 200) as a lubricant was mixed with 50 g of a water-absorbent resin. This mixture was passed through a JIS standard sieve having an opening size of 250 μm. When 50 mass % or more of the resin remains on the sieve, a sieve combination of (A) was used to measure a median particle size. On the other hand, when less than 50 mass % of the resin remains on the sieve, a sieve combination of (B) was used to measure a median particle size.

(A) JIS standard sieves were combined in a downward order of a sieve having an opening size of 710 μm, a sieve having an opening size of 600 μm, a sieve having an opening size of 500 μm, a sieve having an opening size of 400 μm, a sieve having an opening size of 300 μm, a sieve having an opening size of 250 μm, a sieve having an opening size of 150 μm, and a tray.

(B) JIS standard sieves were combined in a downward order of a sieve having an opening size of 400 μm, a sieve having an opening of 250 μm, a sieve having an opening size of 180 μm, a sieve having an opening size of 150 μm, a sieve with an opening size of 106 μm, a sieve with an opening size of 75 μm, a sieve having an opening size of 45 μm, and a tray.

A water-absorbent resin was placed on the uppermost sieve of the combination, and shaken 10 minutes using a Rotap-type shaking machine for classification. After the classification, the mass of the water-absorbent resin remaining on the respective sieves was calculated in terms of mass % based on the total mass of the resin, the values were integrated in an order from the resins with a larger particle size, and thereby the relations between the opening sizes of sieve and integration values of the mass % of the water-absorbent resin remaining on the sieve were plotted on a logarithmic-probability paper. The plots on the logarithmic-probability paper were connected with a straight line, and the particle size corresponding to integrated mass % of 50 mass % was defined as the median particle size.

Example 1

A cylindrical round-bottomed separable flask having an internal diameter of 100 mm was prepared, wherein the flask was equipped with a reflux condenser, a dropping funnel, a nitrogen gas introducing tube, and a stirrer having two steps of four-piece-inclined paddle blades with a blade diameter of 50 mm. In this flask, 300 g of n-heptane was introduced as a hydrocarbon dispersion medium, and 0.74 g of sucrose stearic acid ester (Mitsubishi-Kagaku Foods Corporation; Ryoto Sugar Ester S-370) as a surfactant, and 0.74 g of maleic anhydride-modified ethylene-propylene copolymer (Mitsui Chemicals, Inc.; High Wax 1105A) as a polymeric dispersion agent were added. Under stirring, the temperature was raised to 80° C. to dissolve the surfactant, and thereafter the solution was cooled to 55° C.

Separately, 92.0 g (1.021 mol) of 80 mass %-aqueous acrylic acid solution was weighed in a 500-ml Erlenmeyer flask, and 146.0 g of 21 mass %-aqueous sodium hydroxide solution was added dropwise thereto to carry out 75 mol %-neutralization while cooled from outside. Then, 0.110 g (0.406 mmol) of 2,2'-azobis(2-amidinopropane)dihydrochloride as an azo-based compound, 0.037 g (0.137 mmol) of potassium persulfate as a peroxide, and 0.014 g (0.080 mmol) of ethylene glycol diglycidyl ether as an internal-crosslinking agent were added and dissolved to prepare an aqueous monomer solution.

A used amount A mol of the azo-based compound, a used amount B mol of the peroxide, and a used amount C mol of the internal-crosslinking agent, relative to 100 mol of the water-soluble ethylenically unsaturated monomer used in the polymerization, as well as values of formula (1) and formula (2) were represented in following Table 1.

The aqueous monomer solution was added to the separable flask, and the atmosphere inside the flask was completely purged with nitrogen. Then, the flask was immersed in a water bath at 70° C. to raise the temperature, and polymerization was carried out for 60 minutes.

Subsequently, the temperature of the polymerization reaction mixture was raised with an oil bath at 125° C., and while n-heptane was refluxed by azeotropic distillation of water and n-heptane, 115.9 g of water was removed out of the system. Then, 3.68 g (0.423 mmol) of 2 mass %-aqueous ethylene glycol diglycidyl ether solution as a post-crosslinking agent was added, and retained at 80° C. for 2 hours. Subsequently, after the system was heated with an oil bath at 125° C. to remove the dispersion medium and water out of the system, a drying treatment was carried out under nitrogen stream to obtain 95.1 g of sphere-shaped water-absorbent resin. The properties of the water-absorbent resin were measured by the above-mentioned methods, and the results were shown in Table 1.

Example 2

A cylindrical round-bottomed separable flask having an internal diameter of 100 mm was prepared, wherein the flask was equipped with a reflux condenser, a dropping funnel, a nitrogen gas introducing tube, and a stirrer having two steps of four-piece-inclined paddle blades with a blade diameter of 50 mm. In this flask, 300 g of n-heptane was introduced as a hydrocarbon dispersion medium, and 0.74 g of sucrose stearic acid ester (Mitsubishi-Kagaku Foods Corporation, Ryoto Sugar Ester S-370) as a surfactant, and 0.74 g of maleic anhydride-modified ethylene-propylene copolymer (Mitsui Chemicals, Inc., High Wax 1105A) as a polymeric dispersion agent were added. Under stirring, the temperature was raised to 80° C. to dissolve the surfactant, and thereafter the solution was cooled to 55° C.

Separately, 92.0 g (1.021 mol) of 80 mass %-aqueous acrylic acid solution was weighed in a 500-ml Erlenmeyer flask, and 146.0 g of 21 mass %-aqueous sodium hydroxide solution was added dropwise thereto while cooled from outside. Then, 0.110 g (0.406 mmol) of 2,2'-azobis(2-amidinopropane)dihydrochloride as an azo-based compound, 0.018 g (0.067 mmol) of potassium persulfate as a peroxide, and 0.012 g (0.069 mmol) of ethylene glycol diglycidyl ether as an internal-crosslinking agent were added and dissolved to prepare an aqueous monomer solution for a first stage of polymerization.

The aqueous monomer solution for the first stage was added to the separable flask, and the atmosphere inside the flask was completely purged with nitrogen. Then, the flask was immersed in a water bath at 70° C. to raise the temperature, and a first stage of polymerization was carried out for one hour to obtain a reaction mixture of the first stage.

Additionally, 128.8 g (1.430 mol) of 80 mass %-aqueous acrylic acid solution was weighed in another 500-ml Erlenmeyer flask, and 159.0 g of 27 mass %-aqueous sodium hydroxide solution was added dropwise thereto to carryout 75 mol %-neutralization while cooled from outside. Then, 0.155 g (0.572 mmol) of 2,2'-azobis(2-amidinopropane) dihydrochloride as an azo-based compound, 0.026 g (0.096 mmol) of potassium persulfate as a peroxide, and 0.012 g (0.069 mmol) of ethylene glycol diglycidyl ether as an internal-crosslinking agent were added and dissolved to prepare an aqueous monomer solution for a second stage of polymerization.

A used amount A mol of the azo-based compound, a used amount B mol of the peroxide, and a used amount C mol of the internal-crosslinking agent, relative to 100 mol of the water-soluble ethylenically unsaturated monomer used in the polymerization, as well as values of formula (1) and formula (2) were represented in following Table 1.

The reaction mixture of the first stage was cooled to 26° C., and the aqueous monomer solution for the second stage at the same temperature was added into the system and was absorbed for 30 minutes while the atmosphere inside the flask was completely purged with nitrogen. Then, the flask was again immersed in a water bath at 70° C. to raise the temperature, and a second stage of polymerization was carried out for one hour.

After the second stage of polymerization, the temperature of the polymerization reaction mixture was raised with an oil bath at 125° C., and while n-heptane was refluxed by azeotropic distillation of water and n-heptane, 240.8 g of water was removed out of the system. Then, 4.42 g (0.507 mmol) of 2 mass %-aqueous ethylene glycol diglycidyl ether solution as a post-crosslinking agent was added to carry out post-crosslinking reaction at 80° C. for 2 hours. Subsequently, water and n-heptane were removed by distillation and a drying treatment was carried out to obtain 228.2 g of a water-absorbent resin in the form of agglomerated spherical particles. The properties of the water-absorbent resin were measured by the above-mentioned methods, and the results were shown in Table 2.

Example 3

228.6 g of a water-absorbent resin in the form of agglomerated spherical particles was obtained in the same method as in Example 2 except that the used amount of potassium persulfate as the peroxide in the aqueous monomer solution for the first stage was changed to 0.028 g (0.104 mmol), that the used amount of ethylene glycol diglycidyl ether as the internal-crosslinking agent in the aqueous monomer solution for the first stage was changed to 0.014 g (0.080 mmol), that the used amount of potassium persulfate as the peroxide in the aqueous monomer solution for the second stage was changed to 0.038 g (0.141 mmol), and that the amount of water removed out of the system by azeotropic distillation of water and n-heptane before the post-crosslinking reaction was changed to 243.5 g. The properties of the water-absorbent resin were measured by the above-mentioned methods, and the results were shown in Table 2.

Example 4

227.4 g of a water-absorbent resin in the form of agglomerated spherical particles was obtained in the same method as in Example 3 except that the used amount of potassium persulfate as the peroxide in the aqueous monomer solution for the first stage was changed to 0.037 g (0.137 mmol), that the used amount of ethylene glycol diglycidyl ether as the internal-crosslinking agent in the aqueous monomer solution for the first stage was changed to 0.020 g (0.115 mmol), and that the used amount of potassium persulfate as the peroxide in the aqueous monomer solution for the second stage was changed to 0.052 g (0.192 mmol). The properties of the water-absorbent resin were measured by the above-mentioned methods, and the results were shown in Table 2.

Example 5

227.9 g of a water-absorbent resin in the form of agglomerated spherical particles was obtained in the same method as in Example 3 except that the used amount of potassium persulfate as the peroxide in the aqueous monomer solution for the first stage was changed to 0.073 g (0.270 mmol), that the used amount of ethylene glycol diglycidyl ether as the internal-crosslinking agent in the aqueous monomer solution for the first stage was changed to 0.018 g (0.103 mmol), and that the used amount of potassium persulfate as the peroxide in the aqueous monomer solution for the second stage was changed to 0.103 g (0.381 mmol). The properties of the water-absorbent resin were measured by the above-mentioned methods, and the results were shown in Table 2.

Example 6

228.1 g of a water-absorbent resin in the form of agglomerated spherical particles was obtained in the same method as in Example 3 except that potassium persulfate as the peroxide in the aqueous monomer solution for the first stage was changed to 0.083 g (0.364 mmol) of ammonium persulfate, that the used amount of ethylene glycol diglycidyl ether as the internal-crosslinking agent in the aqueous monomer solution for the first stage was changed to 0.024 g (0.138 mmol), and that potassium persulfate as the peroxide in the aqueous monomer solution for the second stage was changed to 0.116 g (0.508 mmol) of ammonium persulfate. The properties of the water-absorbent resin were measured by the above-mentioned methods, and the results were shown in Table 2.

Comparative Example 1

227.6 g of a water-absorbent resin in the form of agglomerated spherical particles was obtained in the same method as in Example 4 except that the used amount of potassium persulfate as the peroxide in the aqueous monomer solution for the first stage was changed to 0.009 g (0.033 mmol), and that the used amount of potassium persulfate as the peroxide in the aqueous monomer solution for the second stage was changed to 0.013 g (0.048 mmol). The properties of the water-absorbent resin were measured by the above-mentioned methods, and the results were shown in Table 2.

Comparative Example 2

228.3 g of a water-absorbent resin in the form of agglomerated spherical particles was obtained in the same method as in Example 3 except that the used amount of ethylene glycol diglycidyl ether as the internal-crosslinking agent in the aqueous monomer solution for the first stage was changed to 0.008 g (0.046 mmol). The properties of the water-absorbent resin were measured by the above-mentioned methods, and the results were shown in Table 2.

Comparative Example 3

227.8 g of a water-absorbent resin in the form of agglomerated spherical particles was obtained in the same method as in Example 3 except that the used amount of ethylene glycol diglycidyl ether as the internal-crosslinking agent in the aqueous monomer solution for the first stage was changed to 0.046 g (0.264 mmol). The properties of the water-absorbent resin were measured by the above-mentioned methods, and the results were shown in Table 2.

Comparative Example 4

A cylindrical round-bottomed separable flask having an internal diameter of 100 mm was prepared, wherein the flask was equipped with a reflux condenser, a dropping funnel, a nitrogen gas introducing tube, and a stirrer having two steps of four-piece-inclined paddle blades with a blade diameter of 50 mm. In this flask, 300 g of n-heptane was introduced as a hydrocarbon dispersion medium, and 0.74 g of sucrose stearic acid ester (Mitsubishi-Kagaku Foods Corporation, Ryoto Sugar Ester S-370) as a surfactant, and 0.74 g of maleic anhydride-modified ethylene-propylene copolymer (Mitsui Chemicals, Inc., High Wax 1105A) as a polymeric dispersion agent were added. Under stirring, the temperature was raised to 80° C. to dissolve the surfactant, and thereafter the solution was cooled to 55° C.

Separately, 92.0 g (1.021 mol) of 80 mass %-aqueous acrylic acid solution was weighed in a 500-ml Erlenmeyer flask, and 146.0 g of 21 mass %-aqueous sodium hydroxide solution was added dropwise thereto to carry out 75 mol %-neutralization while cooled from outside. Then, 0.110 g (0.407 mmol) of potassium persulfate as a peroxide, and 0.012 g (0.069 mmol) of ethylene glycol diglycidyl ether as an internal-crosslinking agent were added and dissolved to prepare an aqueous monomer solution for a first stage of polymerization.

The aqueous monomer solution for the first stage was added to the separable flask, and the atmosphere inside the flask was completely purged with nitrogen. Then, the flask was immersed in a water bath at 70° C. to raise the temperature, and a first stage of polymerization was carried out for one hour to obtain a reaction mixture of a first stage.

Additionally, 128.8 g (1.430 mol) of 80 mass %-aqueous acrylic acid solution was weighed in another 500-ml Erlenmeyer flask, and 159.0 g of 27 mass %-aqueous sodium hydroxide solution was added dropwise thereto to carryout 75 mol %-neutralization while cooled from outside. Then, 0.155 g (0.573 mmol) of potassium persulfate as a peroxide, and 0.012 g (0.069 mmol) of ethylene glycol diglycidyl ether as an internal-crosslinking agent were added and dissolved to prepare an aqueous monomer solution for a second stage of polymerization.

A used amount B mol of the peroxide, and a used amount C mol of the internal-crosslinking agent, relative to 100 mol of the water-soluble ethylenically unsaturated monomer used in the polymerization, as well as values of formula (1) and formula (2) were represented in following Table 1.

The reaction mixture of the first stage was cooled to 26° C., and the aqueous monomer solution for the second stage at the same temperature was added into the system and was absorbed for 30 minutes while the atmosphere inside the flask was completely purged with nitrogen. Then, the flask was again immersed in a water bath at 70° C. to raise the temperature, and a second stage of polymerization was carried out for one hour.

After the second stage of polymerization, the temperature of the polymerization reaction mixture was raised with an oil bath at 125° C., and while n-heptane was refluxed by azeotropic distillation of water and n-heptane, 261.9 g of water was removed out of the system. Then, 4.42 g (0.507 mmol) of 2 mass %-aqueous ethylene glycol diglycidyl ether solution as a post-crosslinking agent was added to carry out post-crosslinking reaction at 80° C. for 2 hours. Subsequently, water and n-heptane were removed by distillation and a drying treatment was carried out to obtain 228.3 g of a water-absorbent resin in the form of agglomerated spherical particles. The properties of the water-absorbent resin were measured by the above-mentioned methods, and the results were shown in Table 2.

TABLE 1

|  | A | B | C | Formula (1) B/(A + B) | Formula (2) B + 9 × C |
|---|---|---|---|---|---|
| Example 1 | 0.0398 | 0.0134 | 0.00784 | 0.25 | 0.084 |
| Example 2 | 0.0399 | 0.00665 | 0.00563 | 0.14 | 0.057 |
| Example 3 | 0.0399 | 0.0100 | 0.00608 | 0.20 | 0.065 |
| Example 4 | 0.0399 | 0.0134 | 0.00751 | 0.25 | 0.081 |
| Example 5 | 0.0399 | 0.0266 | 0.00702 | 0.40 | 0.090 |
| Example 6 | 0.0399 | 0.0356 | 0.00845 | 0.47 | 0.112 |
| Comparative Example 1 | 0.0399 | 0.00330 | 0.00751 | 0.08 | 0.071 |
| Comparative Example 2 | 0.0399 | 0.0100 | 0.00469 | 0.20 | 0.052 |
| Comparative Example 3 | 0.0399 | 0.0100 | 0.0136 | 0.20 | 0.132 |
| Comparative Example 4 | 0 | 0.0400 | 0.00563 | 1.00 | 0.091 |

Notes)
A, B and C represent used amounts (mol) of an azo-based compound, a peroxide and an internal-crosslinking agent, respectively, relative to 100 mol of a water-soluble ethylenically unsaturated monomer used in the polymerization.

TABLE 2

|  | Median Particle Size (μm) | Water-retention Capacity of Physiological saline (g/g) | Water-absorption Capacity of Physiological saline under Load of 4.14 kPa (ml/g) | Vertical Diffusion Water-Absorption Capacity (ml/g) | Content of Residual Monomers (ppm) |
|---|---|---|---|---|---|
| Example 1 | 120 | 41 | 28 | 5.3 | 64 |
| Example 2 | 410 | 41 | 25 | 5.4 | 94 |
| Example 3 | 430 | 46 | 18 | 7.7 | 72 |
| Example 4 | 420 | 41 | 26 | 10.2 | 63 |
| Example 5 | 420 | 42 | 24 | 9.7 | 57 |
| Example 6 | 410 | 40 | 22 | 9.6 | 53 |
| Comparative Example 1 | 430 | 41 | 25 | 9.1 | 193 |
| Comparative Example 2 | 410 | 45 | 18 | 3.2 | 71 |
| Comparative Example 3 | 430 | 35 | 23 | 9.3 | 69 |
| Comparative Example 4 | 420 | 43 | 13 | 6.9 | 49 |

Absorbent materials and absorbent articles were produced with each of the water-absorbent resins obtained in Examples 2 to 4 and Comparative Example 2 to 4, and were evaluated.

Example 7

An absorbent material core in the form of a sheet having a size of 40 cm×12 cm was prepared by uniformly mixing 12 g of the water-absorbent resin obtained in Example 2 and 12 g of crushed pulp (Rayfloc; manufactured by Rayonier Co., Ltd.) in air sheet-making process. Subsequently, while the absorbent material core was placed between two tissue papers, each of which had the same size as the absorbent material core and a basis weight of 16 g/m², the core was all over pressed with a load of 196 kPa for 30 seconds to prepare an absorbent material. An air-through type porous liquid permeable sheet made of polyethylene-polypropylene, which had the same size as the absorbent material and a basis weight of 22 g/m², was placed on the upper side of the absorbent material, and additionally a liquid impermeable sheet made of polyethylene-polypropylene, which has the same size and the same basis weight as the liquid permeable sheet, was placed on the lower side of the absorbent material, and the absorbent material was sandwiched with them to obtain an absorbent article.

Examples 8 to 9 and Comparative Examples 5 to 7

An absorbent article was obtained in the same method as in Example 7 except that each of the water-absorbent resins obtained in Examples 3 to 4 and Comparative Examples 2 to 4 was used instead of the water-absorbent resin obtained in Example 2. The obtained absorbent articles were each defined as absorbent articles in Examples 8 to 9 and Comparative Example 5 to 7 in order.

Subsequently, the absorbent articles obtained in Examples 7 to 9 and Comparative Examples 5 to 7 were evaluated by the following methods. The results were shown in Table 3.
<Evaluation of Absorbent Article>
(a) Preparation of Test Liquid (Synthetic Urine)

0.780 mass % of NaCl, and 0.022 mass % of $CaCl_2$ and 0.038 mass % of $MgSO_4$ were each dissolved in ion-exchange water, and additionally a small amount of Blue No 0.1 was added thereto to prepare a test liquid (synthetic urine).

(b) Liquid Permeation Time

An absorbent article was firstly placed on a horizontal table. A cylinder for introducing a liquid, having an opening part with an internal diameter of 3 cm, was placed on a central part of the absorbent article. 80 ml of the test liquid was introduced into the cylinder at a time, and simultaneously a time until when the test liquid completely disappeared in the cylinder was measured with a stopwatch and was defined as first liquid permeation time (sec). Subsequently, the cylinder was removed and the absorbent article was stored as it was. After 30 minutes and 60 minutes from the first test liquid introduction, the measurement instrument was also placed on the same part as in the first time and the same operation was carried out to measure second and third liquid permeation times (sec). Total time of the first time to third time was defined as total of liquid permeation time. It can be considered that a shorter liquid permeation time is preferable for an absorbent article.

(c) Re-Wet Amount

After 60 minutes passed from termination of the measurement of the third liquid permeation time, a 10 cm-square-filer paper, whose mass had been previously measured (We (g), about 70 g), was placed near the part of the test liquid introduction on the absorbent article, and a weight, which had a mass of 5 kg and whose bottom surface had a size of 10 cm×10 cm, was placed thereon. After the load for 5 minutes, the mass (Wf (g)) of the filter paper was measured, and the mass increase was defined as a re-wet amount (g). It can be considered that a less re-wet amount is preferable for an absorbent article.

Re-wet Amount(g)=$Wf-We$

TABLE 3

|  | Liquid Permeation Time (sec) | | | | Re-wet Amount (g) |
| --- | --- | --- | --- | --- | --- |
|  | 1 | 2 | 3 | Total |  |
| Exmaple 7 | 26 | 38 | 45 | 109 | 11.7 |
| Exmaple 8 | 25 | 29 | 34 | 88 | 7.1 |
| Exmaple 9 | 23 | 24 | 27 | 74 | 10.8 |
| Comparative Example 5 | 28 | 44 | 62 | 134 | 8.2 |
| Comparative Example 6 | 24 | 27 | 32 | 83 | 25.6 |
| Comparative Example 7 | 25 | 30 | 36 | 91 | 23.2 |

As is apparent from Table 3, absorbent articles of Examples 7 to 9, wherein the water-absorbent resins obtained in Examples 2 to 4 were used, represent superior absorption performance including a shorter liquid permeation time and a less re-wet amount, relative to Comparative Examples 5 to 7.

INDUSTRIAL APPLICABILITY

The water-absorbent resin obtained by the production process of the present invention has superior water-absorption performance including a high water-retention capacity, a high water-absorption capacity under a load and a high vertical diffusion water-absorption capacity, as well as a decreased content of residual monomers, and thus, can be suitably used in absorbent articles such as disposable diapers and sanitary napkins.

DESCRIPTION OF SYMBOLS

100 Measurement device
1 Burette part
10 Burette
11 Air introduction pipe
12 Cock
13 Cock
14 Rubber stopper
2 Conduit
3 Measurement table
4 Measurement part
40 Cylinder
41 Nylon mesh
42 Weight
5 Water-absorbent resin

The invention claimed is:

1. A process for producing a water-absorbent resin comprising:
a reverse-phase suspension polymerization of water-soluble ethylenically unsaturated monomers, and then a post-crosslinking reaction,
wherein the reverse-phase suspension polymerization of water-soluble ethylenically unsaturated monomers is carried out in a hydrocarbon dispersion medium comprising a dispersion stabilizer,
wherein an azo-based compound and a peroxide are combined in the presence of an internal-crosslinking agent in aqueous solution comprising the water-soluble ethylenically unsaturated monomers,
wherein the water-soluble ethylenically unsaturated monomers comprise one or more of the group consisting of (meth)acrylic acid and the salt thereof, 2-(meth)acrylamide-2-methylpropanesulfonic acid and the salt thereof, (meth)acrylamide, N,N-dimethyl(meth)acrylamide, 2-hydroxyethyl (meth)acrylate, N-methylol (meth)acrylamide, polyethylene glycol mono(meth) acrylate; N,N-diethylaminoethyl(meth)acrylate, N,N-diethylaminopropyl(meth)acrylate and diethylaminopropyl (meth)acrylamide, as well as the quaternary compounds thereof,
wherein the following formulae are satisfied:

$$0.25 \leq B/(A+B) \leq 0.50 \qquad (1),$$

$$0.055 \leq B + 9 \times C \leq 0.120 \qquad (2), \text{ and}$$

0.0005 mol≤$B$≤0.10 mol, wherein the A is representative of the amount of the azo-based compound in mol; the B is representative of the amount of the peroxide in mol; and C is representative of the amount of the internal-crosslinking agent in mol, relative to 100 mol of the water-soluble ethylenically unsaturated monomers in the reverse-phase suspension polymerization step,
wherein the post-crosslinking reaction is carried out by adding a post-crosslinking agent, and
wherein the water-absorbent resin satisfies all of the following characteristics (A) to (D):
(A) a water-retention capacity of physiological saline of 36 to 60 g/g,
(B) a water-absorption capacity of physiological saline under a load of 4.14 kPa, of 15 ml/g or higher,
(C) a vertical diffusion water-absorption capacity of 4.0 ml/g or higher, and
(D) a content of residual monomers of 180 ppm or lower.

2. The process for producing a water-absorbent resin according to claim 1, wherein the azo-based compound is at least one selected from the group consisting of 2,2'-azobis (2-amidinopropane) dihydrochloride, 2,2'-azobis{2-[1-(2-hydroxyethyl)-2-imidazolin-2-yl]propane} dihydrochloride, and 2,2'-azobis[N-(2-carboxyethyl)-2-methylpropionamidine] tetrahydrate.

3. The process for producing a water-absorbent resin according to claim 1, wherein the peroxide is at least one selected from the group consisting of potassium persulfate, ammonium persulfate, sodium persulfate and hydrogen peroxide.

4. The process for producing a water-absorbent resin according to claim 1, wherein the internal-crosslinking agent is at least one selected from the group consisting of (poly) ethylene glycol diglycidyl ether, (poly)propylene glycol diglycidyl ether, (poly)glycerin diglycidyl ether and N,N'-methylenebis(meth)acrylamide.

5. The process for producing a water-absorbent resin according to claim 1, wherein the azo-based compound and the peroxide simultaneously coexist in an aqueous solution before the start point of polymerization in the reverse-phase suspension polymerization step.

6. The process for producing a water-absorbent resin according to claim 1,
wherein the azo-based compound is at least one selected from the group consisting of 2,2'-azobis(2-amidinopropane) dihydrochloride, 2,2'-azobis{2-[1-(2-hydroxyethyl)-2-imidazolin-2-yl]propane} dihydrochloride, and 2,2'-azobis[N-(2-carboxyethyl)-2-methylpropionamidine] tetrahydrate,
wherein the peroxide is at least one selected from the group consisting of potassium persulfate, ammonium persulfate, sodium persulfate and hydrogen peroxide, and
wherein the internal-crosslinking agent is at least one selected from the group consisting of (poly)ethylene glycol diglycidyl ether, (poly)propylene glycol diglycidyl ether, (poly)glycerin diglycidyl ether and N,N'-methylenebis(meth)acrylamide.

7. The process for producing a water-absorbent resin according to claim 1, wherein the azo-based compound is 0.005 to 1 mol relative to 100 mol of the water-soluble ethylenically unsaturated monomers in the reverse-phase suspension polymerization step.

8. The process for producing a water-absorbent resin according to claim 1, wherein the internal-crosslinking agent is 0.001 to 0.13 mol relative to 100 mol of the water-soluble ethylenically unsaturated monomers in the reverse-phase suspension polymerization step.

9. The process for producing a water-absorbent resin according to claim 1, wherein the post-crosslinking agent is 0.001 to 1 mol relative to 100 mol of the water-soluble ethylenically unsaturated monomers in the reverse-phase suspension polymerization step.

10. The process for producing a water-absorbent resin according to claim 1,
wherein the azo-based compound is 0.005 to 1 mol relative to 100 mol of the water-soluble ethylenically unsaturated monomers in the reverse-phase suspension polymerization step,
wherein the internal-crosslinking agent is 0.001 to 0.13 mol relative to 100 mol of the water-soluble ethylenically unsaturated monomers in the reverse-phase suspension polymerization step, and
wherein the post-crosslinking agent is 0.001 to 1 mol relative to 100 mol of the water-soluble ethylenically unsaturated monomers in the reverse-phase suspension polymerization step.

11. The process for producing a water-absorbent resin according to claim 1,
wherein the internal-crosslinking agent is at least one selected from the group consisting of (poly)ethylene glycol diglycidyl ether and (poly)propylene glycol polyglycidyl ether.

12. The process for producing a water-absorbent resin according to claim 1,
wherein the post-crosslinking agent is at least one selected from the group consisting of (poly)ethylene glycol diglycidyl ether, (poly)glycerin diglycidyl ether, (poly)glycerin triglycidyl ether, (poly)propylene glycol polyglycidyl ether and (poly)glycerol polyglycidyl ether.

13. The process for producing a water-absorbent resin according to claim 1,
wherein the reverse-phase suspension polymerization is carried out in multi-stages having two or more stages.

* * * * *